(12) United States Patent
Yamazaki et al.

(10) Patent No.: US 7,744,594 B2
(45) Date of Patent: Jun. 29, 2010

(54) CATHETER FOR TREATING OF ARRHYTHMIA

(75) Inventors: Yoshiharu Yamazaki, Otsu (JP); Motoki Takaoka, Otsu (JP)

(73) Assignee: TORAY Industries, Inc., Tokyo (JP)

( * ) Notice: Subject to any disclaimer, the term of this patent is extended or adjusted under 35 U.S.C. 154(b) by 1549 days.

(21) Appl. No.: 10/522,788

(22) PCT Filed: Aug. 20, 2003

(86) PCT No.: PCT/JP03/10503

§ 371 (c)(1),
(2), (4) Date: Jan. 28, 2000

(87) PCT Pub. No.: WO2004/017850

PCT Pub. Date: Mar. 4, 2004

(65) Prior Publication Data

US 2005/0203597 A1      Sep. 15, 2005

(30) Foreign Application Priority Data

Aug. 20, 2002   (JP)   ............................. 2002-239407
Dec. 27, 2002   (JP)   ............................. 2002-379830

(51) Int. Cl.
   *A61B 18/18*   (2006.01)
   *A61M 29/00*   (2006.01)
(52) U.S. Cl. ..................... 606/41; 606/192; 604/96.01
(58) Field of Classification Search ......... 607/101–105; 606/41, 48–50, 192–195; 604/96.01, 103
See application file for complete search history.

(56) References Cited

U.S. PATENT DOCUMENTS

| | | | | |
|---|---|---|---|---|
| 4,921,483 A | * | 5/1990 | Wijay et al. ............... | 604/103.1 |
| 4,946,440 A | * | 8/1990 | Hall ....................... | 604/164.09 |
| 4,955,377 A | * | 9/1990 | Lennox et al. ............... | 607/105 |
| 5,041,089 A | * | 8/1991 | Mueller et al. ......... | 604/103.09 |
| 5,171,305 A | | 12/1992 | Schickling et al. .......... | 604/271 |
| 5,498,261 A | * | 3/1996 | Strul ........................... | 606/29 |
| 5,643,209 A | * | 7/1997 | Fugoso et al. ............. | 604/96.01 |
| 5,676,654 A | * | 10/1997 | Ellis et al. .................... | 604/103 |
| 5,762,630 A | | 6/1998 | Bley et al. .................. | 604/164 |
| 6,102,908 A | * | 8/2000 | Tu et al. ........................ | 606/41 |
| 6,491,710 B2 | * | 12/2002 | Satake ......................... | 606/191 |
| 6,500,174 B1 | * | 12/2002 | Maguire et al. ............... | 606/41 |

(Continued)

FOREIGN PATENT DOCUMENTS

JP    2000-107296 A    4/2000

(Continued)

*Primary Examiner*—Michael Peffley
(74) *Attorney, Agent, or Firm*—Kubovcik & Kubovcik

(57) ABSTRACT

A catheter for treating arrhythmia comprises a catheter shaft of a double-cylinder structure where an inner shaft is slidably inserted in an outer shaft, a balloon installed so as to straddle between the tip portion of the inner shaft and the tip portion of the outer shaft, a pair of high frequency current-carrying electrodes of which at least one electrode is provided inside the balloon, and a temperature sensor for monitoring the temperature in the balloon. The front edge portion of the balloon at least in a deflated state protrude from the tip portion of the inner shaft. Alternatively, a tube that is more flexible than the inner shaft is provided on the tip portion of the inner shaft.

3 Claims, 11 Drawing Sheets

U.S. PATENT DOCUMENTS 6,652,515 B1 11/2003 Maguire et al. .............. 606/41
2002/0165535 A1 11/2002 Lesh et al. .................. 606/41

FOREIGN PATENT DOCUMENTS

JP 2002-11101 A 1/2002
JP 2002-78809 A 3/2002
WO 00/42934 A1 7/2000

* cited by examiner

CATHETER FOR TREATING OF ARRHYTHMIA

This application is a 371 of international application PCT/JP2003/010503, which claims priority based on Japanese patent application Nos. 2002-239407 and 2002-379830 filed Aug. 20 and Dec. 27, 2002, respectively, which are incorporated herein by reference.

FIELD OF THE INVENTION

The present invention relates to a catheter for use in the treating of arrhythmia, and more specifically, to a catheter for use in the treating of arrhythmia whereby a balloon is caused to contact closely to the cause of arrhythmia and localized ablation is carried out using high frequency heating.

BACKGROUND ART

In recent years, it has been learnt that many of the causes of arrhythmia (or arterial fibrillation) exist within a pulmonary vein, and for this reason, if the cause of the problem is electrically isolated, arrhythmia can be cared. In accordance with this, currently popular methods of treatment adopt a metallic electrode catheter comprised of a chip of 4 mm in length to contact the ostia of pulmonary vein, where the pulmonary vein joins the left atrium, and by repeated ablation achieved using high frequency current while moving sequentially around the circular ostia of pulmonary vein, the pulmonary vein constituting the cause of arrhythmia is electrically isolated from the atrium.

However, in the above-described treatment if sequential point-contact ablation around the circular ostia of pulmonary vein is not carried out several tens of times, it is impossible to ablate the entire surroundings of each ostium; accordingly, the method in question is problematic with respect to the exceptional amount of time required. A method of proposing contact between a balloon of a high frequency current type of balloon catheter and the ostia of pulmonary vein, and ablation by high frequency current has been proposed in Japanese Patent Laid Open No. 2002-78809 as a means of achieving this treatment in a short period of time. Using this balloon catheter, there is no need to repeatedly carry out ablation in the same way as with conventional catheters, and complete circumferential ablation of the ostia of pulmonary vein is possible through a single high frequency current-carrying process; accordingly, it became possible to greatly reduce the time required for treatment while simultaneously reducing the stress placed on the patient.

When treatment of arterial fibrillation using high frequency current type of balloon catheter as explained above is carried out, it is necessary for the balloon on the distal end of the catheter to be inserted into the affected area of the heart. And in the insertion procedure, the balloon is guided to the heart via the femoral vein and the inferior vena cava; furthermore, it is introduced to the left atrium through the septum by puncturing the interatrial septum via the right atrium. Once inside the left atrium, the balloon is inflated, and wedged into the ostia of pulmonary vein. However, when this type of catheter is passed through blood vessel and heart, the balloon thereof may unintentionally interfere with vessel junctions and the interior of the heart on the way to pulmonary vein, and this has resulted in damaging the body parts such as vessels and heart. It is not always the case, therefore, that the catheter is smoothly inserted without problems occurring. Accordingly, while the balloon catheter as described above does allow ablation to be carried out in a short period of time, problems remain to be solved with regard to the insertion process.

Another problem associated with the high frequency current type balloon catheter as explained above is softening of the catheter shaft as a result of the heat generated through high frequency current-carrying. And when softening of the shaft occurs in this way, the balloon pressing against the ostia of pulmonary vein can slip away because of the influence of pulmonary venous pressure. For this reason, cooling of the interior of conventional high frequency current type of balloon catheter is carried out through the circulating coolant water. However, in order for this cooling to be achieved, a pipe for circulating the coolant water must be inserted into the catheter shaft; accordingly, the catheter shaft becomes thicker, not only impairing the handling of the catheter thereof, but also increasing the stress placed on the patient.

Furthermore, the balloon temperature of high frequency current type of balloon catheter as explained above is raised to between 50° C. and 70° C. in order for ablation to be carried out. Although temperature sensors are provided inside the balloons in order to maintain the temperature at a constant level, the balloon temperature can not be accurately measured when the configuration and structure of the temperature sensor is not correct.

DISCLOSURE OF THE INVENTION

The main object of the present invention is to provide a high frequency current type of balloon catheter for use in the treating of arrhythmia with improved ease of insertion.

Another object of the present invention is to provide a catheter for use in the treating of arrhythmia with improved wedge performance of the balloon to the ostia of pulmonary vein.

A further object of the present invention is to provide a catheter for use in the treating of arrhythmia with an ability to suppress softening of the shaft thereof without a need for circulation of cooling water.

Another object of the present invention is to provide a catheter for use in the treating of arrhythmia capable of accurately detecting the temperature within the balloon thereof.

Other objects of the present invention will be clarified by way of the specific examples below.

In order to achieve the main object explained above, the catheter for use in the treating of arrhythmia according to the present invention comprises a catheter shaft having a double-cylinder structure wherein an inner shaft is slidably inserted into an outer shaft, a balloon attached between the tip of the inner shaft and the tip of the outer shaft in a straddling state, a pair of high frequency current-carrying electrodes of which at least one electrode is disposed inside the balloon, and a temperature sensor monitoring the temperature inside the balloon; and is configured such that in the deflated state of the balloon, at least the front edge of the balloon protrudes from the tip of the inner shaft towards the front thereof.

In accordance with the fact that the front edge of the balloon protrudes from the tip of the inner shaft at least under the deflated condition, the present invention advances with the edge of the soft balloon as its tip, ensuring that insertion takes place smoothly without damaging the inferior vena cava or the interior of the heart.

Furthermore, another catheter for use in the treating of arrhythmia according to the present invention comprises a catheter shaft having a double-cylinder structure wherein an inner shaft is slidably inserted into an outer shaft, a balloon attached between the tip of the inner shaft and the tip of the outer shaft in a straddling state, a pair of high frequency current-carrying electrodes of which at least one electrode is disposed inside the balloon, and a temperature sensor monitoring the temperature inside the balloon; and is configured such that a tube that is softer than the inner shaft is provided at the tip of the inner cylinder tube, and the length of the tube is 50 mm or less.

In accordance with the fact that a tube that is softer than the inner shaft is provided at the tip of the inner tube, when inserting the catheter for the treating of arrhythmia, the soft tube constitutes the tip of the catheter as it advances, ensuring that insertion takes place smoothly without damaging the inferior vena cava or the inside of the heart.

Furthermore, specific examples of the configuration of the present invention in order to achieve other objects are provided hereinafter in the description of the preferred embodiments.

BEST MODE FOR CARRYING OUT THE INVENTION

In order to facilitate understanding of the present invention, the embodiments thereof will hereinafter be described.

Figure 1:
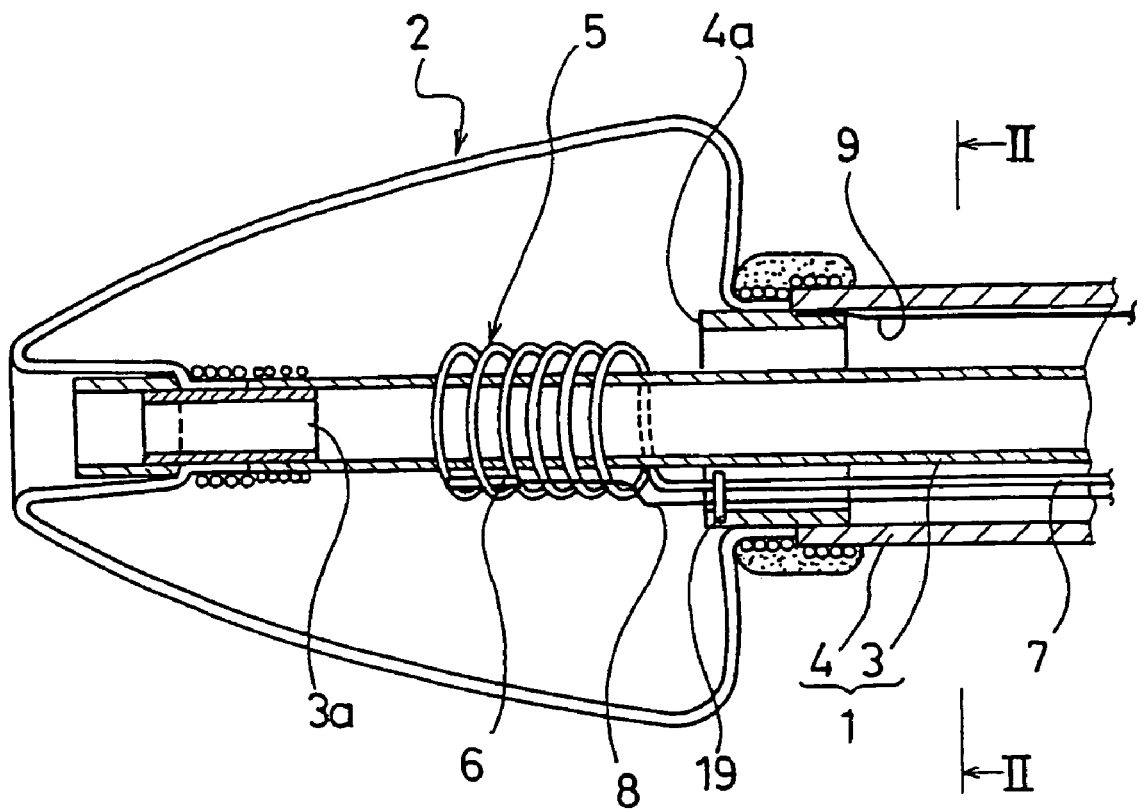
FIG. 1 is a cross-section view showing a critical part at the tip of a catheter for use in the treating of arrhythmia in accordance with an embodiment of the present invention.
Figure 2:
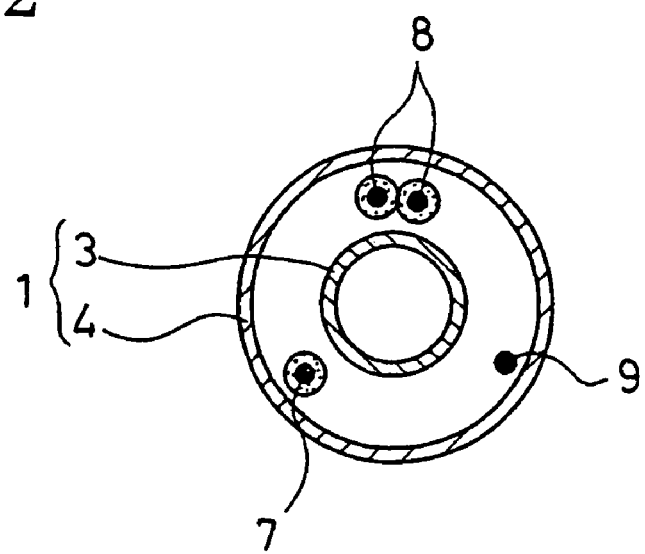
FIG. 2 is a cross-section taken in the plane II-II shown in FIG. 1.
Figure 3:
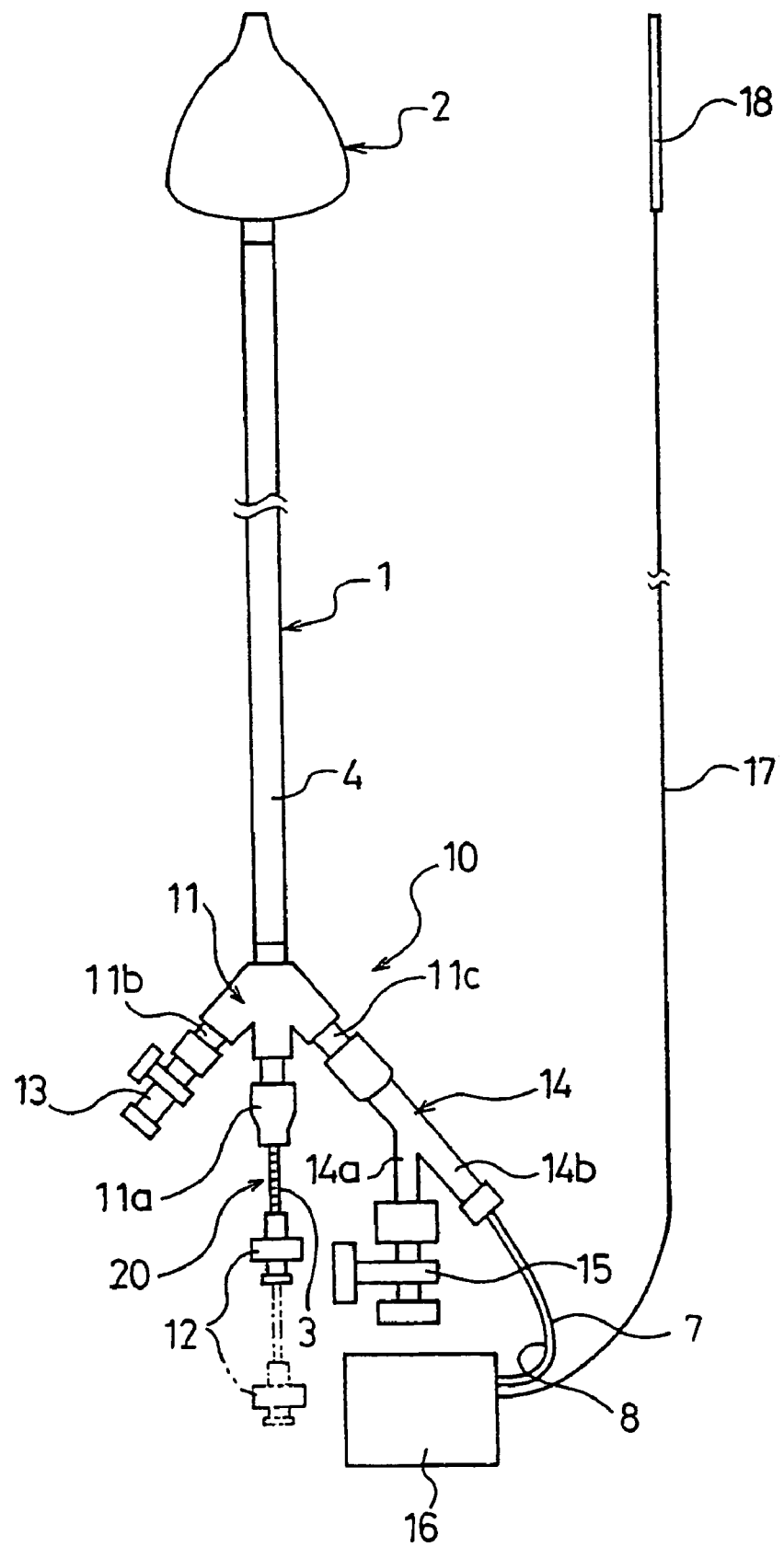
FIG. 3 is a schematic view showing the configuration of the entire catheter shown in FIG. 1.

FIG. 1 through FIG. 3 show a series of catheters for use in the treating of arrhythmia in accordance with the present invention.

In the catheters from these figures, a balloon 2 capable of being inflated and deflated is mounted to the tip of a catheter shaft 1. The catheter shaft 1 comprises a double-cylinder structure with an inner shaft 3 and an outer shaft 4, and the inner shaft 3 is inserted in such a way that longitudinal sliding thereof with respect to the inner shaft 3 and the outer shaft 4 is possible. The inner shaft 3 and the outer shaft 4 are both made from a radiopaque resin material and with antithrombogenic properties, and metal pipes 3a, 4a with radiation shielding properties are connected to the tips of each shaft 3, 4. The balloon 2 is fixed at the front end thereof to the metal pipe 3a and at the rear end thereof to the metal pipe 4a, straddling the opening between both metal pipes 3a, 4a.

The metal pipes 3a, 4a are provided for identifying the positions of the tip of the inner shaft 3 and the tip of the outer shaft 4 when viewed using x-rays, and this allows the position of the balloon 2 to be determined. However, it is not necessary that the ends of the balloon 2 are always disposed on the metal pipes 3a, 4a, and direct mounting on the inner shaft 3 and the outer shaft 4 is acceptable. In other words, it is acceptable for these ends to correspond with the tips of inner shaft 3 and outer shaft 4 that include ancillary items such as metal pipes 3a, 4a. Hereinafter in this specification, the terms "tip of the inner shaft 3" and "tip of the outer shaft 4" will, unless otherwise specified, not refer directly to the tips of inner shaft 3 and outer shaft 4, but will also include ancillary items such as metal pipes 3a, 4a attached thereto.

The front end of the balloon 2 extends forward from the fixed section attached to the tip of the inner shaft 3, and having protruded from the tip thereof, inverts to extend rearward. Accordingly, this configuration ensures that the front edge of the balloon 2 is always disposed more forward than the tip of the inner shaft 3 when, at the very least, the balloon 2 is deflated.

A high frequency current-carrying electrode 5 comprising a coil body made by winding a wire in a spiral configuration is mounted around the tip of the inner shaft 3 that faces the inside of the balloon 2. A high frequency current-carrying electrode 18 is mounted outside of the balloon 2 as a counter electrode for the high frequency current-carrying electrode 5 (see FIG. 3). The high frequency current-carrying electrode 18 is attached to the surface of the patient's body during ablation treatment. Furthermore, a temperature sensor 6 is fixed in the high frequency current-carrying electrode 5 installed inside of the balloon 2, and the temperature within the balloon 2 is monitored using this temperature sensor 6.

An electrode lead wire 7 and a temperature sensor lead wire 8 are connected to the high frequency current-carrying electrode 5 and the temperature sensor 6 respectively, and after being secured of each to the metal pipe 4a using a retainer 19, are extended to a operation section 10 mounted on the rear end of the catheter shaft 1 along the clearance between the inner shaft 3 and the outer shaft 4, and are connected to a high frequency generating device 16 provided in the operation section 10 (see FIG. 3). In addition, anti-elongation string 9 is inserted in parallel into the catheter shaft 1. The front end of the string 9 is secured to the tip of the outer shaft 4 through entrapment by the metal pipe 4a, and the rear end thereof is secured to the operation section 10. The anti-elongation string 9 prevents elongation of the catheter shaft 1 softened through heating, and as a result, favorable operation of the catheter can be maintained.

A four-way connector 11 is secured to the rear end of the outer shaft 4. Furthermore, the rear end of the inner shaft 3 extends outward to pass through a central branch pipe 11a of the four-way connector 11, and the extended end section is connected to a operation handle 12. When the inner shaft 3 is inserted axially using the operation handle 12, the tip of the balloon 2 advances forward in an axial direction, allowing the external diameter thereof to be changed. A scale 20 is provided on the surface of the rear end of the inner shaft 3, and using the scale 20, the degree of sliding (or length) of the inner shaft 3 is measured and the outer diameter of the balloon 2 can be determined. The scale 20 may directly indicate the degree of sliding of the inner shaft 3, or alternatively, and indicate the outer diameter of the balloon 2 calculated based on the degree of sliding of the inner shaft 3.

Of the left and right side branch pipes 11b, 11c of the four-way connector 11, the side junction pipe 11b is connected to a two-way connector 13, and the other side junction pipe 11c is connected to a Y-shaped connector 14. Furthermore, of the two junction pipes 14a, 14b of the Y-shaped connector 14, the junction pipe 14a is connected to a two-way connector 15, and the electrode lead wire 7 and the temperature sensor lead wire 8 pass through the other junction pipe 14b. The electrode lead wire 7 and temperature sensor lead wire 8 extending from the junction pipe 14b are each connected to the high frequency generating device 16.

With regard to the two two-way connectors 13, 15 described above, one supplies a dilute contrast media solution to the balloon 2 by using a supply pump, while the other extracts the dilute contrast media solution by using the action of a suction pump, thus allowing the pressure inside the balloon 2 to be adjusted. Furthermore, the electrode lead wire 7 is connected to the high frequency generating device 16, as is an electrode lead wire 17 extending from the high frequency current-carrying electrode 18. The high frequency generating device 16 provides high frequency power to the high frequency current-carrying electrodes 5, 18 via the electrode lead wires 7, 17 respectively; accordingly, high frequency waves are transmitted between the electrodes 5, 18 and the temperature of the dilute contrast media solution contained within the balloon 2 rises as a result of high frequency induced heating and Joule heating, realizing circumferential ablation of the area of the patient's body in contact with the balloon 2.

Figure 4:
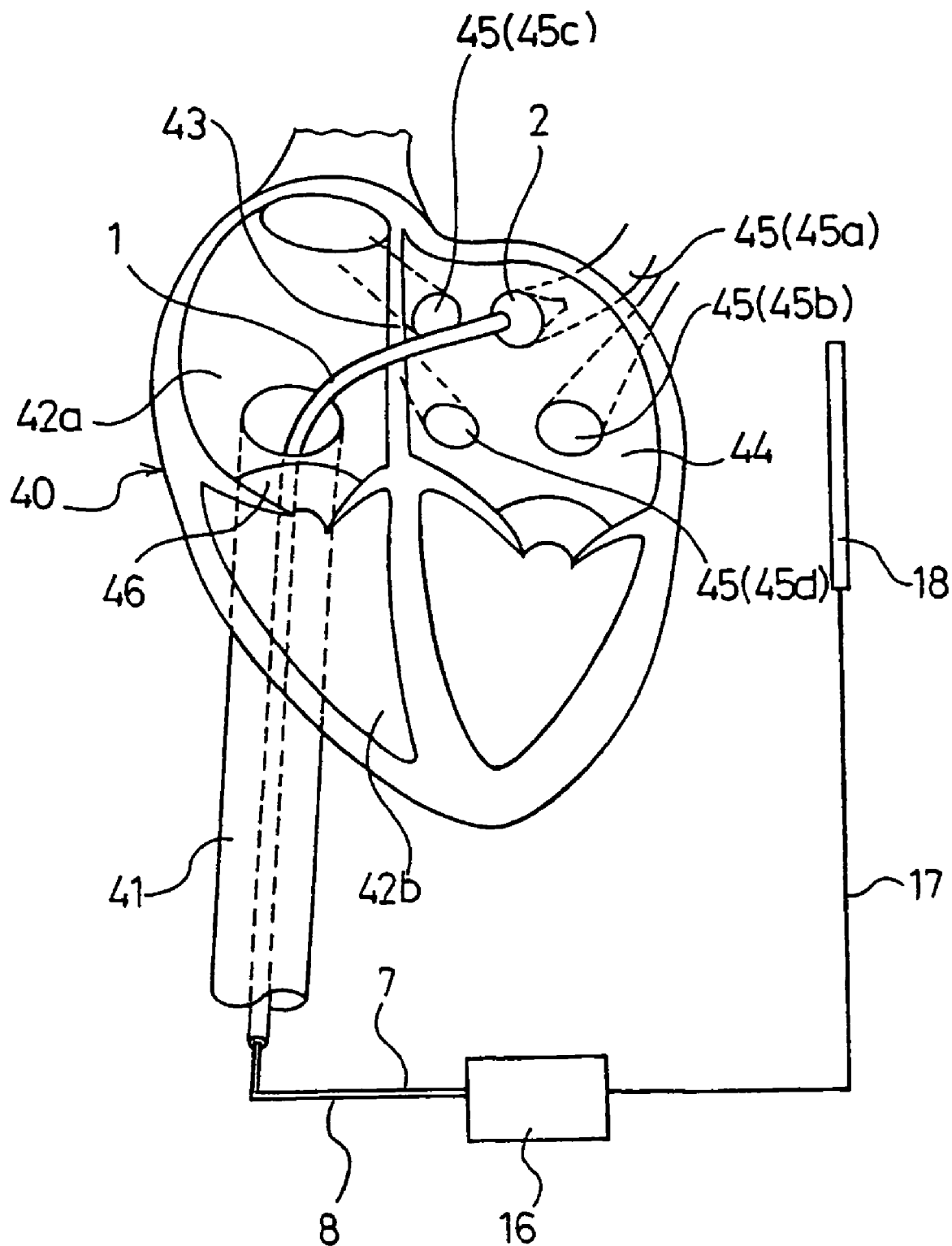
FIG. 4 is a schematic view showing an example of a condition when the catheter for use in the treating of arrhythmia in accordance with the present invention is used.

FIG. 4 shows a schematic diagram of the situation upon treating of arrhythmia using the above-described catheter.

Generally, a guide wire is used as a secondary means when inserting a catheter into the patient. A guide wire is initially inserted in advance of catheter insertion, and following this, the catheter is inserted and guided by the guide wire. The ideal guide wire for use with the catheter in accordance with the present invention is described hereinafter.

Referring to FIG. 4, before catheter insertion takes place, a guide wire (not shown) is inserted from the patient's inner thigh via the inferior vena cava 41 to the right atrium 42a of the heart 40. It then passes from the right atrium 42a to the left atrium 44 via the interatrial septum 43. After setting of the guide wire has been completed, the deflated balloon 2 is inserted into the left atrium 44 of the heart 40 via the inferior vena cava 41 as the catheter's inner shaft 3 is guided by the guide wire. Once inside the left atrium 44, dilute contrast media solution is introduced by either the two-way connector 13 or the two-way connector 15 to inflate the balloon 2, causing the inflated balloon 2 to come into contact with and wedge one of the four openings (45a, 45b, 45c, 45d) for the pulmonary vein 45.

Since the front edge of the soft balloon 2 protrudes from the front edge of the inner shaft 3 in the catheter in accordance with the present invention, insertion thereof into the inferior vena cava 41 and the heart 40 with the front edge of the balloon 2 as its leading edge can proceed smoothly with no interference with blood vessel junctions and the inside the heart and no other infliction of injury.

When the balloon 2 makes close contact with the ostia of pulmonary vein as described above, high frequency power with a frequency selected from the 1 to 2,450 MHz range is supplied to the high frequency current-carrying electrodes 5, 18 by the high frequency generating device 16; accordingly, high frequency waves pass between the high frequency current-carrying electrodes 5, 18 and the temperature of the dilute contrast media solution contained within the balloon 2 rises, realizing circumferential ablation of the ostia of pulmonary vein in contact with the balloon 2. As a result of this ablation, the ostia of pulmonary vein alone is electrically isolated from the left atrium 44.

Furthermore, during the course of this ablation treatment, the temperature of the dilute contrast media solution contained inside the balloon 2 is monitored by the temperature sensor 6, and based on the detection signal thereof, the high frequency generating device 16 adjusts the output of high frequency electric power, such that the temperature of the balloon 2 maintains within the 50° C. to 70° C. range. In addition, the high frequency generating device 16 has a function that facilitates monitoring of the impedance between the high frequency current-carrying electrodes 5, 18, and time period of applying the high frequency power is adjusted such that the impedance between the high frequency current-carrying electrodes 5, 18 is maintained within a specific range.

The above-described catheter for use in the treating of arrhythmia has been described in terms of an embodiment of the present invention. Including this embodiment, the present invention is configured as described hereinafter. In the present invention, the balloon material has elastic recovery properties, and while the possession of antithrombogenic properties alone is acceptable, the utilization of polyurethane polymer materials is particularly preferable. The examples of polyurethane polymer materials include thermoresin polyurethanes, polyether polyurethane ureas, fluoropolyether polyurethane ureas, polyether polyurethane urea resins, polyether polyurethane urea amides, and the like.

It is preferable that the polyurethane polymer material has, in particular, an instantaneous recovery rate of 90% or greater at the modulus of 300% elongation, and that the strength thereof be between 12 and 24 MPa. The term "instantaneous recovery rate at the modulus of 300% elongation" refers to a value indicating the ratio of the original length to the length after elongation to 300% (i.e., a magnitude of 4) by a tensile tester, retention of this extension for 5 seconds, removal of all tension, and instantaneous recovery. This value is obtained by the following equation:

Instantaneous recovery rate for 300% elongation (%)= (original length/length after instantaneous recovery)×100

When the polyurethane material has an instantaneous recovery rate of 90% or greater at the modulus of 300% elongation, the balloon will rapidly return to its deflated condition after inflation is released, thus reducing the time taken to complete the treatment and also the stress placed on the patient. Furthermore, when the tensile strength is less than 12 MPa, the balloon may rupture upon inflation; when it is greater than 24 MPa, it may not be possible to conveniently carry out the required inflation and elongation.

The shape of the balloon is such that, as illustrated in the embodiment shown in FIG. 1, when under the deflated condition at the very least, the front edge thereof protrudes beyond the front edge of the inner shaft. With the balloon shaped to ensure that the front edge thereof protrudes from the front edge of the inner shaft, passage of the catheter from the inferior vena cava to the heart can proceed smoothly with no interference with blood vessel junctions, the interior of the heart, tissues, other organs, and the like and no other infliction of injury. Furthermore, damage to the wall of the left atrium upon operation therein can be prevented.

It is preferable that the thickness of the balloon membrane be between 100 and 300 µm when deflated. With a thickness of 100 µm or greater, it is possible to hold a specific shape during inflation. Furthermore, with the thickness at 300 µm or less, easy elongation thereof will be assured. A thickness in the above-specified range ensures that passage through blood vessels in addition to expansion and ablation in the pulmonary vein can be easily achieved.

A balloon shape that allows close contact to be made with the ostia of pulmonary vein is preferable. For example, it is preferable that the balloon shape is conical with a smaller diametric portion at the front and gradually increasing in diameter towards the rear thereof The use of a conical balloon ensures that complete circumferential contact can be easily made with the affected area of the ostia of pulmonary vein.

Figure 12:
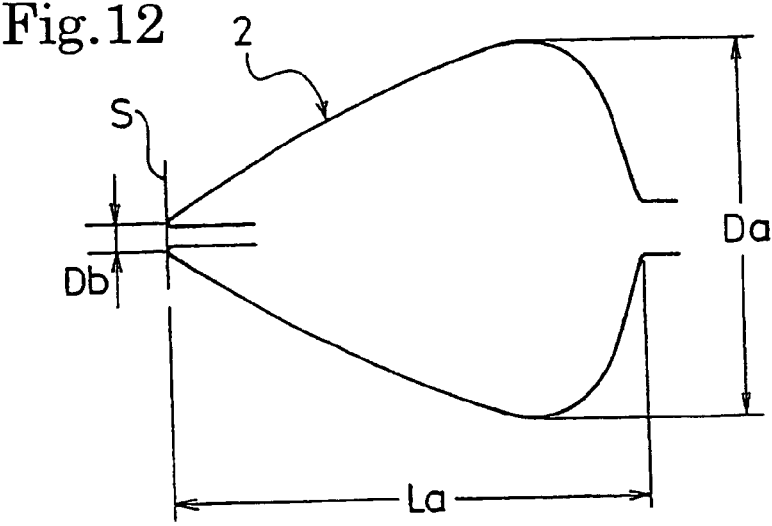
FIG. 12 is a schematic view related to the dimensions upon inflation of the balloon used in the embodiment of FIG. 1.

In terms of the dimensions of the balloon when inflated to form conical, it is preferable that the large diameter Da and a small diameter Db as shown in FIG. 12 be such that the ratio thereof Da/Db is in the range of 5 to 12. The diametrical ratio ensures the highest level of contact with the affected area when the ratio Da/Db is less than 5 or greater than 12, closeness of the contact is impaired. The term "large diameter" as used here refers to the diameter of the portion of the balloon with the largest size upon inflation. Similarly, the term "small diameter" refers to the diameter obtained on plane S which is perpendicular to the axial direction as shown in FIG. 12 when the edge at the smaller end is incident upon the plane S. Furthermore, it is preferable that, when the balloon is inflated to its conical shape, the length La in the axial direction is between 10 and 40 mm. When La is within this range, the balloon will exhibit favorable operability within the atria and ventricles.

Figure 7:
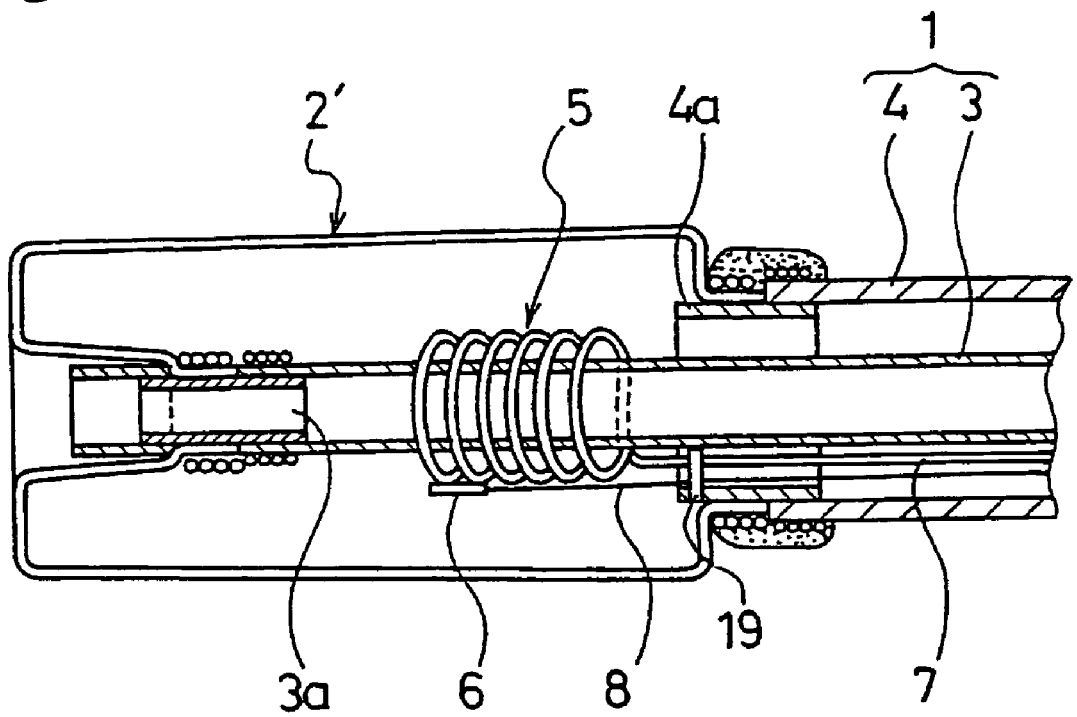
FIG. 7 is a cross-section view showing a critical part at the tip of a catheter for use in the treating of arrhythmia in accordance with yet another embodiment of the present invention.
Figure 8:
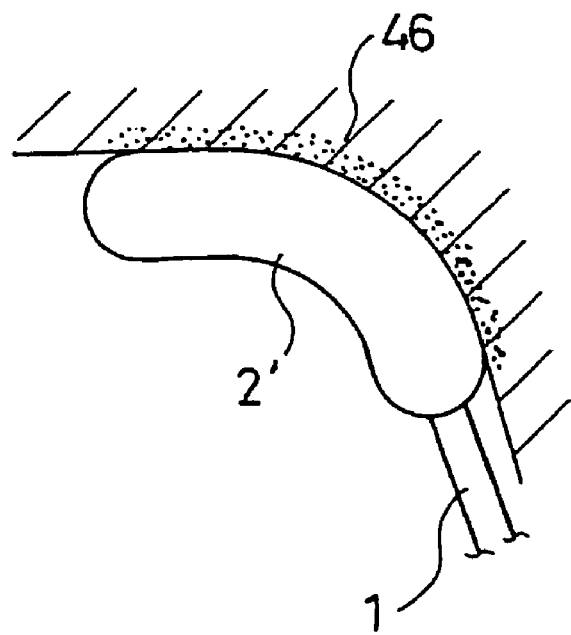
FIG. 8 is a schematic view showing the state when the balloon of a catheter for use in the treating of arrhythmia in accordance with yet another embodiment of the present invention is inflated.

As shown in FIG. 7, the inflated balloon may also be given a long cylindrical shape. More preferable is the curved cylinder illustrated in FIG. 8.

balloon 2' with a cylindrical shape as shown in FIG. 7 and FIG. 8 is preferably used when the affected area is not the entrance for the pulmonary vein 45, but rather when performing ablation over a wide area at the tricuspid valve 46 between the right atria 42a and 42b. In particular, when using the outer curved side of the curved cylindrical balloon 2' as shown in FIG. 8, contact can be made easily with the inner wall of the tricuspidal valve 46; accordingly, more favorable ablation is realized. Furthermore, by using the inner curved side of the curved cylindrical balloon 2', contact can be made easily with the isthmus between the superior and inferior vena cava and the right atrium, and similarly, more favorable ablation is realized.

Figure 13:
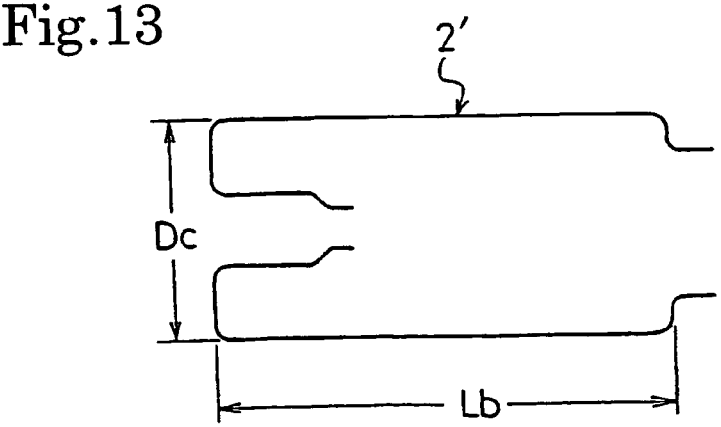
FIG. 13 is a schematic view related to the dimensions upon inflation of the balloon used in the embodiment of FIG. 7.

In the same way as for the conical balloon, it is preferable that the thickness of the balloon membrane upon deflation be within the 100 to 300 µm range for the cylindrical balloon 2'. In terms of dimensions upon inflation, furthermore, it is preferable from the point of view of ease of insertion and operation within the heart that, as shown in FIG. 13, the length Lb in the longitudinal direction be within the 10 to 40 mm range, and that the diameter Dc be within the 5 to 20 mm range. In addition, in order to achieve favorable contact with balloon 2', it is preferable that the ratio (Lb/Dc) between the length Lb and the diameter Dc be between 1.5 and 8.0.

Figure 10:
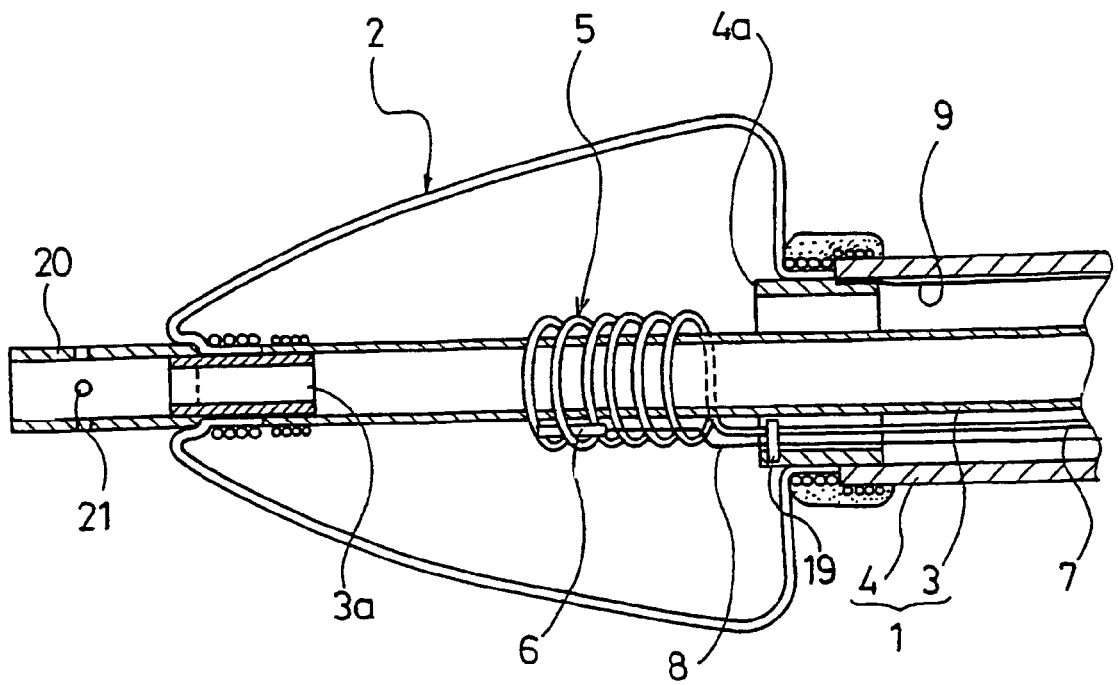
FIG. 10 is a cross-section view showing a critical part at the tip of a catheter for use in the treating of arrhythmia in accordance with yet another embodiment of the present invention.

In addition to implementing a specific balloon shape as described above, for preventing damage to blood vessels and other tissues when inserting the catheter from the inferior vena cava to the heart a tube 20 comprising a resin having a higher level of flexibility than the inner shaft 3 may be attached to the tip of the inner shaft 3 as shown in FIG. 10 preventing damage to blood vessels etc. when inserting the catheter from the inferior vena cava to the heart. The shape of the balloon when such a tube is implemented may be conical or cylindrical.

In the embodiment of FIG. 10, the tube 20 is linked to the metal pipe 3a having radiation shielding properties and mounted on the tip of the inner shaft 3. The front edge of the balloon 2 is secured to this metal pipe 3a. Although it is acceptable for the length of the tube 20 to be such that it extends at least 1 mm from the tip of the inner shaft 3 (or metal pipe 3a), an allowable length of 50 mm or less is favorable. When the balloon 2 is under the inflated state and contact with the ostia of pulmonary vein with the protrusion length of 50 mm or more, the tip of the tube 20 penetrates deep into the pulmonary vein, and the liquid introduced during ablation may enter the lungs.

It is preferable for one or a multiplicity of side holes 21 to be provided on the wall of the tube. By providing these side holes 21, the dilute contrast media solution introduced into the catheter can be distributed, allowing favorable fluoroscopic image around the catheter tip and making it easier to confirm contact between the balloon 2 and the ostia of pulmonary vein. Furthermore, although the tube 20 is mounted onto the tip of the inner shaft 3 using the metal pipe 3a as illustrated in the figure, the tube 20 may be formed together with the inner shaft 3 into a single component with a hardness gradient. In this way, the single component with a hardness gradient and comprising both tube and inner shaft together with a hardness gradient, eliminates the need for a connection between tips via the metal pipe, improving productivity.

Although it is sufficient for the material forming the catheter's inner shaft and outer shaft in the present invention to exhibit antithrombogenic properties within blood vessels, it is preferable that a resin with a low specific inductive capacity be used. In terms of the value of the specific inductive capacity, it is acceptable that the value if 3 or less when measured at a frequency of 1 MHz. The specific inductive capacity referred to herein is measured in accordance with JIS K 6911 specifications.

Fluororesin (polytetrafluoroethylene, polytetrafluoroethylene hexafluoro-propylene copolymers, tetrafluoroethylene fluoro-alkyl ether copolymers), polyethylene, polyimide resin, polyamide resin, thermoresin elastomers (polyamide, styrene, polyester, or olefin base), polypropylene, and methylpentene polymers, etc. are identified as low specific inductive capacity resin for use in the catheter shaft.

By forming the catheter shaft using such a resin with the specific inductive capacity of 3 or less at a frequency of 1 MHz, it is possible to eliminate the need for the cooling water circulation tube required for cooling of the catheter shaft in the prior art. Accordingly, the catheter shaft can be reduced in diameter, improving the handling of the catheter.

It is preferable that the tip of the inner shaft and the outer shaft are each attached by fitting to a metal pipe with radiation shielding properties, and that the front edge and rear edge of the balloon are secured on this metal pipe. By providing a metal pipe with radiation shielding properties on each of the tips of the inner shaft and the outer shaft in this way, the position of the metal pipe can be clearly distinguished in x-ray images, allowing easy confirmation of the position of the balloon within the heart. The metal used for the radiation shielding pipe is not particularly limited as long as it exhibits a low transparency to ionizing radiation; however, the metals preferably used include gold, platinum, stainless steel, and Ti—Ni alloys.

The catheter of the present invention provides a pair of high frequency current-carrying electrodes to facilitate the raising of temperature through high frequency induction heating and Joule heating, and at least, one of the electrodes thereof is provided on the inner side of the balloon. It is acceptable for the other electrode to be attached to the surface of the patient's body or so as to form a pair within the balloon.

Figure 5:
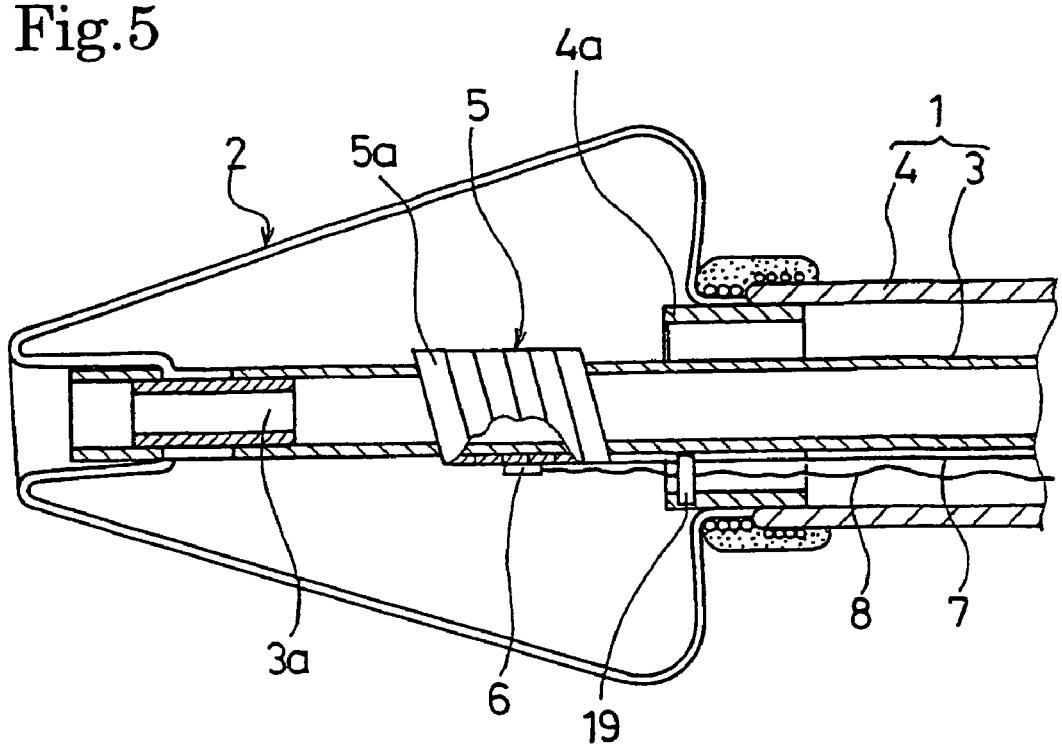
FIG. 5 is a cross-section view showing a critical part at the tip of a catheter for use in the treating of arrhythmia in accordance with another embodiment of the present invention.

No specific restrictions apply to the shape of the electrode from the pair of high frequency current-carrying electrodes that is provided inside the balloon; however, it is preferable for example that this be formed around the outside of the inner shaft using a coil body upon which metal wire is wrapped in a spiral configuration. In the case of such a coil shaped electrode, it is acceptable to use a coil body 5 to which the flat metal wire 5a of the section shown in the embodiment of FIG. 5 has been wrapped in a spiral configuration. And it is further preferable that the thickness of the flat metal wire 5a be between 0.05 and 0.2 mm.

By forming the high frequency current-carrying electrode 5 from coil body of a flat metal wire 5a, it is possible to realize not only a small coil-body diameter, but also a balloon having a small diameter when it is deflated; accordingly, the ease of insertion of the catheter into the patient and operation therein is improved. If the thickness of the metal wire were less than 0.05 mm, it would be difficult to maintain the strength required as an electrode; furthermore, if the thickness thereof were in excess of 0.2 mm, the above-described reduction of diameter would be difficult to achieve.

Figure 6:
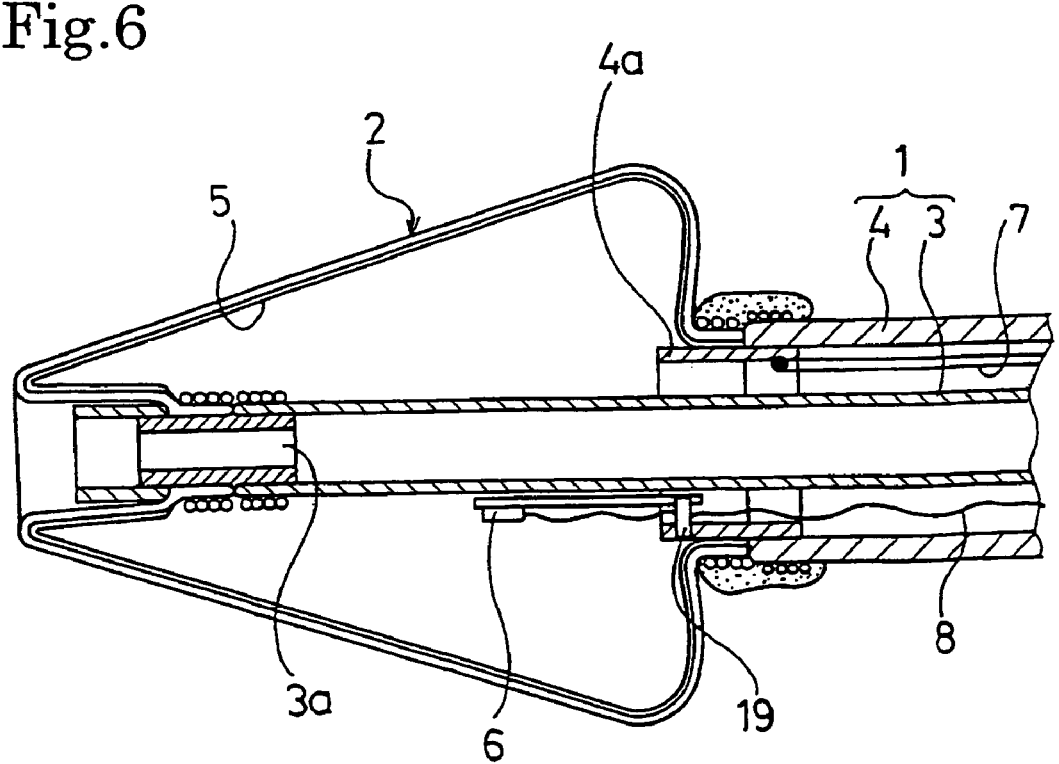
FIG. 6 is a cross-section view showing a critical part at the tip of a further catheter for use in the treating of arrhythmia in accordance with yet another embodiment of the present invention.

The high frequency current-carrying electrode disposed inside the balloon may be formed as a film applied onto the inner circumference of the balloon as shown in the embodiment of FIG. 6. By forming the high frequency current-carrying electrode 5 as a film applied onto the inner circumference of the balloon in this way, heating can be applied uniformly and evenly over the entire contact area, avoiding partially insufficient or excess ablation, regardless of the way in which the balloon is in contact with the affected area of the ostia of pulmonary vein. Furthermore, in contrast to cases where a coil shaped electrode is used, the outer diameter of the deflated balloon can be made significantly smaller.

It is preferable that the thickness of the planer electrode described above be between 5 and 20 µm, and the examples of the electrically conductive material used for the planer electrode include gold, silver, platinum, copper, and aluminum etc. can be identified. Method for forming the planer electrode may be chosen from vapor deposition, plating, painting, and other similar methods of the electrically conductive material. Furthermore, it is acceptable that the above-described planer electrode be formed so as to coat at least half of the front edge of the balloon, and there is no need for this electrode to coat the complete inner surface thereof.

The other electrode from the pair of high frequency current-carrying electrodes is provided through attachment to the surface of the patient's body. In order to facilitate easy attachment of this high frequency current-carrying electrode to the patient's body surface, it is preferable that a sheet-type planer electrode be used. Although a minimum number of planer electrodes of one is acceptable for this purpose, it is also acceptable for a multiplicity thereof, and preferably two or three, to coat an equal surface area by each planer electrode. By using multiple planer electrodes, sufficient electrical contact can be maintained with curved surfaces of patients' bodies.

It is preferable that the surface area per planer electrode be at least 80 $cm^2$. By maintaining a surface area of 80 $cm^2$ or greater, high frequency electric power can evenly be widely distributed over the electrode surface with no concentration, reducing the danger of the patient's body being subjected to burn damage. However, in order to ensure ease of application to the patient's body, it is preferable that the maximum surface area of the planer electrode be 600 $cm^2$.

Figure 9:
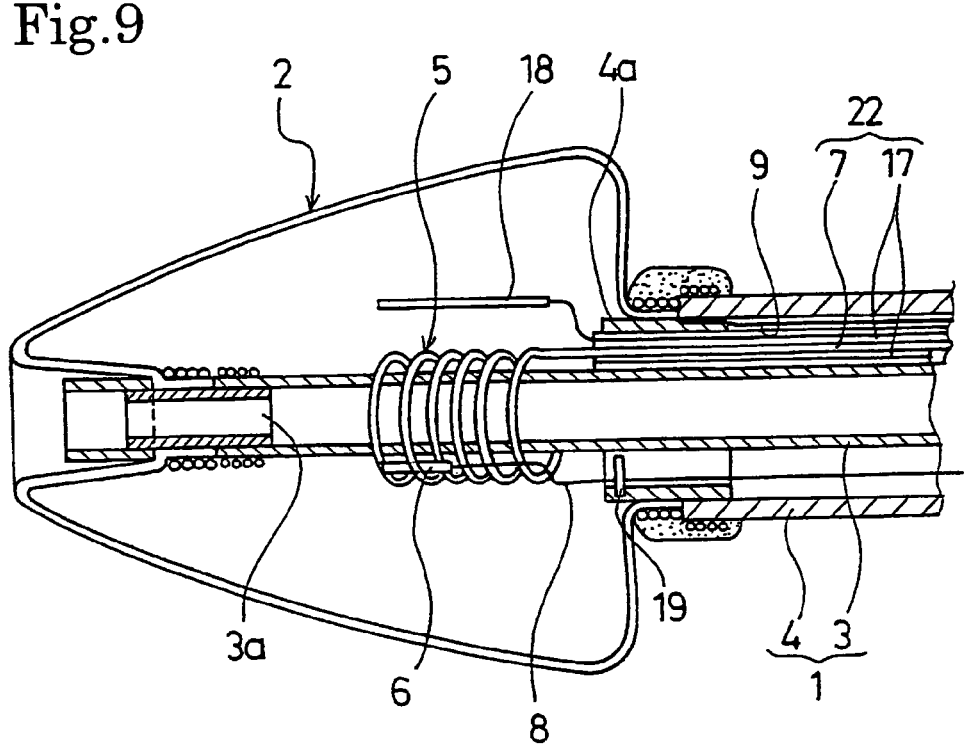
FIG. 9 is a cross-section view showing a critical part at the tip of a catheter for use in the treating of arrhythmia in accordance with yet another embodiment of the present invention.

It is also acceptable for the other electrode described above to be provided within the balloon. In the embodiment of FIG. 9, one electrode 5 of a pair of high frequency current-carrying electrodes comprises a coil body formed from conductive wires as described above; furthermore, the other electrode 18 comprises a flat plate or mesh of electrically conductive material. In addition to being mutually electrically insulated, the lead wires 7, 17 of the electrodes 7, 17 are combined within a coaxial cable construction 22 and extend to the rear end of the catheter shaft 1 via the clearance between the inner shaft 3 and the outer shaft 4.

By combining the two lead wires 7, 17 in a coaxial cable construction 22 in this way, the pair of high frequency current-carrying electrodes 5, 18 can be provided within the balloon 2; accordingly, it is possible to restrict the high frequency transmission between the high frequency current-carrying electrodes 5, 18 to the inside of the balloon 2. Furthermore, as it is not necessary for the electrode 18 to be applied to the surface of the patient's body and because the high frequency transmission between the high frequency current-carrying electrodes 5, 18 is restricted to the inside of the balloon 2, leakage of high frequency waves to the exterior is reduced.

In the present invention, the material forming the electrode lead wires connected to the high frequency current-carrying electrodes are not particularly limited as long as they are characterized by low heat generation and low energy loss upon high frequency current-carrying. The examples of the materials used for the lead wire include gold, silver, copper, aluminum, and platinum etc.

Furthermore, it is preferable that over the path of connection to the electrode, the electrode lead wires are coated with a shielding resin having low dielectric constant. It is preferable that the resin used for shielding has a dielectric constant of 3 or less when measured at a frequency of 1 MHz. When a shielding resin having a high dielectric constant is used, it may become difficult to restrain the heating of the catheter shaft that originates in the high frequency current-carrying electrodes. In such a case, a cooling-water circulation tube would become necessary, leading to the problem of an increased catheter shaft diameter. Fluororesins (PTFE, FEP, PFA), polyethylene, polystyrene, and polyurethane, etc. can be identified as examples of resins for use as the shielding material.

In the catheter of the present invention, it is preferable that ablation treatment is realized by providing a frequency selected from the range of 1 to 2,450 MHz to a pair of high frequency current-carrying electrodes. However, relatively low frequencies from the above-described frequency range such as 13.56 MHz, are characterized in that exothermic occurs in a fat layer, which shows a high resistance. In addition, these relatively low frequencies from the frequency band have low levels of directionality with respect to fat layers and considerable time is required for heating, leading to the problem of poor heating efficiency. Accordingly, it is more preferable for efficient heating over a short period of time to be realized using high frequencies in the 100 to 2,450 MHz range. In addition, this also allows the generation of high temperatures to be limited to the areas where it is required.

It is acceptable that the temperature sensor used in the present invention be capable of measuring the temperature within the balloon; however, it is preferable that a thermocouple be used for this purpose. The temperature data monitored by the temperature sensor is provided to the high frequency generating device in the form of feedback. The high frequency generating device outputs power to the high frequency current-carrying electrodes based on the temperature data received as feedback so as to maintain the temperature of the interior of the balloon within the required range.

No specific requirements apply to the position of the temperature sensor within the balloon; however, it is preferable that this be disposed more towards the front edge of the balloon than the central longitudinal point thereof. By positioning the temperature sensors closer to the balloon's front edge, the output thereof will be affected to the minimal degree by the charging and discharging, via the inlet for the low temperature dilute contrast media solution provided at the rear of the balloon for the purpose of mixing.

Furthermore, it is more preferable that the temperature sensor be disposed close to the axis of the balloon. Since the actions of inflation and deflation take place about the central axis of the balloon, there would be increased danger of contact between the sensor and the balloon membrane and the balloon suffering damage during these actions if the temperature sensor were to be disposed away from this axis in the radial direction.

Furthermore, the temperature sensor may, as illustrated in the embodiment of FIG. 1, be provided in a fixed condition in the high frequency current-carrying electrode. The temperature of the solution within the balloon as described above is not necessarily uniform over the entire balloon: accordingly, if the temperature sensor is provided in a fixed condition within the high frequency current-carrying electrode and is capable of directly detecting the temperature thereof, the relationship between the electrode temperature and the temperature of the balloon tip region making contact with the affected area can be measured in advance in order to facilitate accurate temperature monitoring.

It is preferable that the material of the lead wires connected to the temperature sensor is a conductor allowing transmission of the electrical signal corresponding to the temperature monitored by the temperature sensor. Platinum, tungsten, copper, alloys of these metals, and chromel, etc. can be identified as examples thereof. In order to prevent the occurrence of short circuits with the lead wires of the high frequency current-carrying electrode within the catheter shaft, it is preferable that the lead wires of the temperature sensor be coated with a shielding material. In the same way as for the electrode lead wires, it is preferable that this shielding material be a resin with a specific inductive capacity of 3 or less at a frequency of 1 MHz. As with the electrode lead wires, if the shielding material were to have a higher specific inductive capacity, it would become difficult to restrain the heating of the catheter shaft caused by high frequency current-carrying, and the resultant need for a cooling-water circulation tube would result in the catheter shaft requiring a larger diameter. Fluororesins (PTFE, FEP, PFA), polyethylene, polystyrene, and polyurethane, etc. can be identified as examples of resins for use as the shielding material.

It is preferable for both the above-described high frequency current-carrying electrodes and temperature sensor to be secured by a securing tool via the corresponding lead wires. Although no specific requirements apply to these securing tools, clamp or band type members formed of resin, aramid fiber, or the like may be preferably used. Securing of the high frequency current-carrying electrodes and the temperature sensor through the action of securing tools ensures that, even after repeated inflation and deflation of the balloon, the high frequency current-carrying electrodes and the temperature sensor will not be displaced from their original positions and that suitable heating and temperature monitoring can be realized.

As described above, in the catheter for use in the treating of arrhythmia of the present invention, the catheter shaft softens and elongates during usage as a result of heating occurring due to high frequency current-carrying; accordingly, extreme difficulty is experienced during operations such as balloon inflation, balloon deflation, and balloon extraction. In order to suppress this softening and elongation, it is effective to dispose inextensible string in parallel to the catheter shaft. With regard to the mounting of the inextensible string, it is preferable for one end thereof to be secured to the tip of the outer shaft and for the other end thereof to be secured to the operation section provided in the rear end of the outer shaft.

Polyimide fiber, polyester fiber, polyethylene fiber, carbon fiber, and aramid fiber can be identified as examples of the preferable material for use as the anti-elongation string. In addition, it is acceptable for the diameter of the anti-elongation string to be in the 0.05 to 1 mm range. If the string were to be less than 0.05 mm in thickness, it would be difficult to assure the strength required for reliable usage of the catheter as described above. Furthermore, it the string were to be thicker than 1 mm, disposition thereof between the outer shaft and inner shaft would be problematic.

By disposing the catheter shaft and the inextensible string in parallel, it is possible to eliminate the operational difficulty associated with softening and elongation of the shaft. Although a forced cooling device may be provided to eliminate the operational difficulty associated with softening and elongation of the string, as described above, the provision thereof would result in the catheter shaft becoming larger in diameter, and this solution is not therefore preferable.

Figure 11:
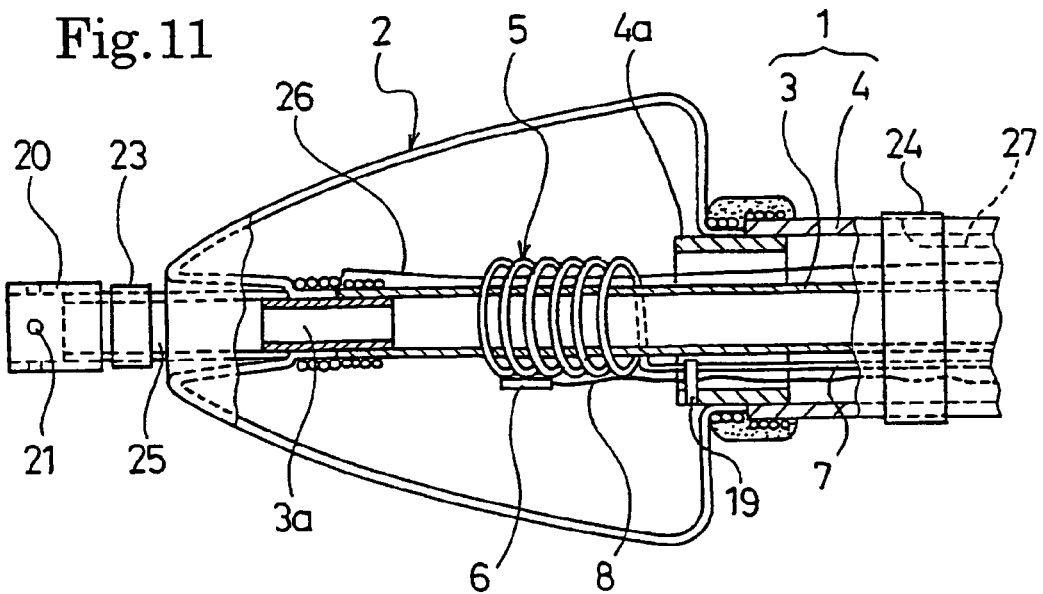
FIG. 11 is a cross-section view showing a critical part at the tip of a catheter for use in the treating of arrhythmia in accordance with yet another embodiment of the present invention.

After removal of the catheter for the treating of arrhythmia in accordance with the present invention, following the completion of ablation treatment, a different catheter for the detection of potential is inserted, the potential of the ablated area subjected to ablation is measured, and the completeness of ablation treatment is confirmed. However, the repeated action of insertion of a catheter for the confirmation of potential subjects the patient to extreme stress. In the embodiment of FIG. 11, this type of patient stress is reduced by providing the catheter for the treating of arrhythmia with a device for the measurement of potential at locations where ablation has been completed.

The catheter of FIG. 11 provides potential detection electrodes 23, 24 on the tip of the inner shaft 3 and the tip of the outer shaft 4 at the opposite sides of the balloon 2 so as to enable measurement of the potential of the ablation area with which the balloon 2 makes contact. The potential detection electrode 23 at the tip of the inner shaft 3 links the resin pipe 25 to the radiation shielding metal pipe 3a linked to the inner shaft 3 and is secured on the resin pipe 25. Also attached to the tip of the resin pipe 25 is the soft tube 20 illustrated in FIG. 10.

Furthermore, the potential detecting electrode 24 disposed at the tip of the outer shaft 4 is directly secured to the outer shaft 4. Each of the lead wires 26, 27 connected to the potential detecting electrodes 23, 24, respectively, is coated with an electrically-insulating coating material and is connected to a potentiometer (not shown) disposed at the rear end of the catheter shaft 1 via the clearance between the inner shaft 3 and the outer shaft 4. Rather than passing through the clearance between the inner shaft 3 and the outer shaft 4, it is acceptable for the route of passage of the lead wires 26, 27 to the rear end of the catheter shaft 1 may be such that the lead wire 26 to passes through the material thickness of the inner shaft 3, and the lead wire 27 passes through the material thickness of the outer shaft 4. As the potential detecting electrodes are intended to directly measure the potential of the ablation area, disposition of them at both sides of the balloon 2 as shown in the embodiment of FIG. 11 is not absolutely necessary and disposition of both thereof at either end is acceptable. It is also acceptable for three or more potential detection electrodes to be employed where so required.

As described above, when using the catheter for the treating of arrhythmia in accordance with the present invention, a guide wire with a suitable balance of rigidity and flexibility is used as an auxiliary tool of a guide. The guide wire ensures that the catheter can be inserted efficiently into the patient with no damage done to blood vessels or tissue, and by contributing to catheter rigidity, it plays an important role in maintaining the catheter in the required position.

Figure 14:
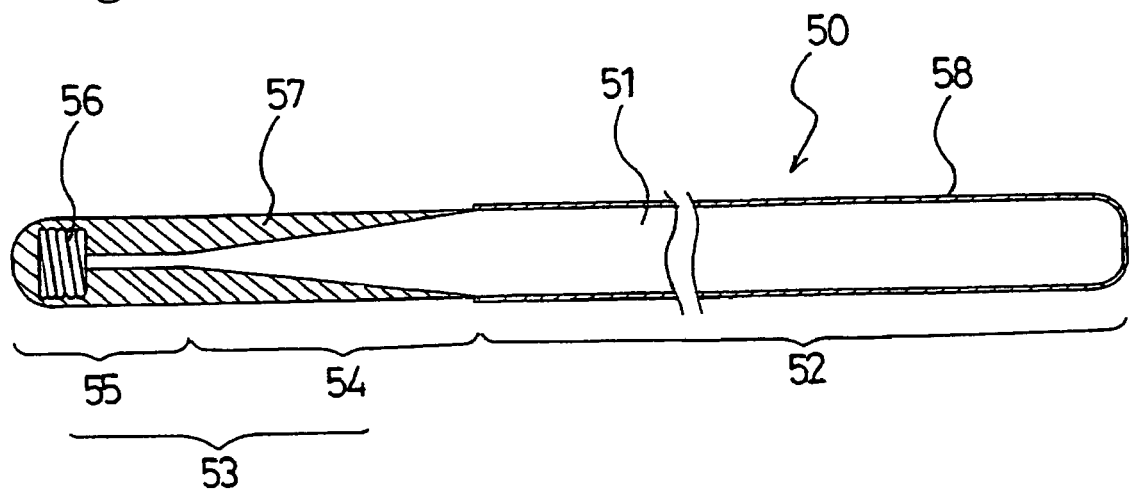
FIG. 14 is a cross-section view showing a guide wire used in the catheter for use in the treating of arrhythmia in accordance with the present invention and excluding the intermediate portion thereof.
Figure 15:
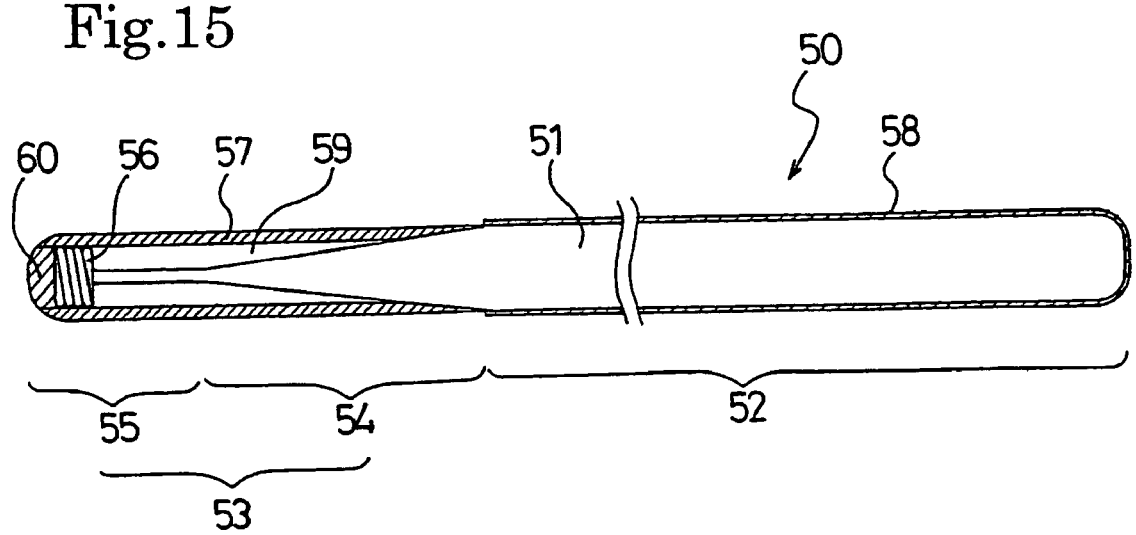
FIG. 15 is a cross-section view showing a guide wire used in another embodiment of the catheter for use in the treating of arrhythmia in accordance with the present invention and excluding the intermediate portion thereof.

The guide wires shown in FIG. 14 and FIG. 15 are each example of suitable guide wires for use in the high frequency ablation treatment with the catheter of the present invention.

The guide wire 50 illustrated in FIG. 14 is formed by extending a single metal wire 51 with a suitable balance of rigidity and flexibility, over the entire length. The majority of the length of the metal wire 15 corresponds to the operation section 52, and a flexible section 53 is formed at the tip thereof. The flexible section 53 comprises a taper section 54 wherein the diameter of the metal wire 51 from the operation section 52 becomes gradually smaller and a small diameter section 55 with the same diameter as the small end of the taper section 54 and attached thereto. In addition, a contrast marker 56 is attached to the tip of the small diameter section 55. The contrast marker 56 is formed as a metal wire coil with radiation shielding properties wound in a spiral configuration or as a braided section and is welded to the tip of the small diameter section. The outer diameter thereof is either equal to or slightly smaller than the diameter of the operation section 52.

The flexible section 53, including the contrast marker 56, is completely coated by a resin 57 with low specific inductive capacity such that the external diameter thereof is approximately equal to that of the operation section 52. In terms of this resin with low specific inductive capacity, a resin with a specific inductive capacity value of 3 or less at a frequency of 1 MHz is used. Further, the operation section 52 is coated on the surface with a thin film of resin 58 such as fluororesin or silicone with low resistance to sliding. The above-described resin 57 of low specific inductive capacity may be coated on the entire surface of the guide wire 50 as well as the flexible section 53.

In the guide wire 50 as shown in FIG. 15, the low specific inductive capacity resin 57 pre-formed into a tube coats the flexible section 53 forming a hollow section 59 inside thereof, and resin 60 is provided at the tip thereof as a sunken cap. With the exception of these differences, all other sections have substantially the same configuration as the embodiment shown in FIG. 14.

As the catheter for use in the treating arrhythmia in accordance with the present invention utilizes high frequency waves, the tip of the metal guide wire is also heated when these waves are transmitted thereby, and ablation of blood vessels and tissue outside the affected area may be performed by this tip. However, as the flexible section 53 is coated by resin 57, if the guide wire 50 as shown in FIG. 14 or FIG. 15 is used, the problem of ablation of sections other than that affected area can be eliminated. Furthermore, by providing the guide wire 50 with a suitable degree of rigidity, it is possible to augment the rigidity of the catheter shaft softened through heating, improving the performance thereof.

It is preferable that the metal used in the above-described guide wire be stainless steel wire, piano wire, or a shape memory alloy etc. Of these, stainless steel wires are more preferable, specifically SUS301H, SUS301SEH, or similar varieties with high rigidity. Although no specific requirements apply to the diameter of the metal wire, it is preferable that the diameter of the operation section be between 0.5 and 1.5 mm from the point of view of attaining suitable stiffness for convenient operation. With regard to the flexible section, in order to improve flexibility and ensure that no damage is done to blood vessels and other tissues even when contact is made, it is acceptable for the diameter of the small diameter section to be between 0.05 and 0.30 mm, and more preferably in the range 0.05 to 0.15 mm.

Furthermore, the length of the small diameter section is in the range 10 to 300 mm; and more preferably in the range 30 to 100 mm. The small diameter section need not necessarily have a straight shape, and it is acceptable for a coil shape to be adopted in order to contribute to increased flexibility. It is preferable that the coil diameter of the coiled shape be equal to or less than the diameter of the operation section. Furthermore, the length of the taper section is in the range 20 to 300 mm; and more preferably in the range 20 to 100 mm is preferable.

As a result of x-ray transparency, a contrast marker facilitates confirmation of the position of the guide wire by fluoroscopy. Specifically, the contrast marker allows confirmation of the arrival of the tip of the guide wire in the target area. No specific requirements apply to the metal used as the contrast marker. The examples of the metal suitable for the contrast marker include gold, platinum, silver, bismuth, tungsten, and alloys wherein these metals comprise the main component can be identified as suitable. It is acceptable for the coil, mesh, or tube comprising this metal to be welded to the tip of the small diameter section or to be press-fitted therein for the purpose of mounting.

It is important that the range of the flexible section coat the low specific inductive capacity resin, including the contrast marker section. Coverage by this low specific inductive capacity resin prevents the tip of the guide wire from being heated. It is preferable that the length of the flexible section coated with a resin be between 50 and 200 mm. Furthermore, it is preferable that the thickness of the coating resin be between 0.1 and 0.5 mm. The method for coating a resin is not particularly limited as long as it fits the purpose of the present invention. The examples of the method include, direct coating and coating through the formation of a tube are acceptable.

In terms of usable resins, poly-para-xylylene, polyurethane, polyamide, PVC, polyester, polyacrylamide, polyolefin, polypropylene, polyvinyl acetate, silicon, and polyester can be identified as being suitable, and poly-para-xylylene, polyurethane, and silicon are preferable in accordance with their relatively low effect on the human body.

If a hydrophilic coating is also formed on the surface of the above-described resin, handling and insertion of the guide wire can be further improved. This hydrophilic coating can be easily formed through hydrophilic processing of the surface of the resin. In terms of hydrophilic processing, it is preferable that contact between a compound containing at least two isocyanate radicals and the surface of the resin be carried out, and furthermore, that reaction with an hydrophilic polymer be realized.

Although no specific requirements apply to the compound containing at least two isocyanate radicals, it is specifically preferable that diphenylmethane diisocyanate, diisocyanatohexane, xylene diisocyanate, triphenylmethane diisocyanate, toluylene diisocynate, etc. be used.

It is preferable that methyl ethyl ketone, trichloroethylene, chloroform, or dichloromethane etc. be used as the solvent for dissolution of the compound containing at least two isocyanate radicals. It is acceptable that the above-described compound containing at least two isocyanate radicals be dissolved in this solvent to form a solution, and for this solution to be brought into contact with the resin surface. Following this, a reaction with the hydrophilic polymer is realized, and in terms of the hydrophilic polymer, polyvinyl alcohol, polyethylene oxide, polyethylene glycol, methyl vinyl ether maelic anhydride copolymer, and polyvinyl-polypyrrolidone etc. can be specifically identified.

By performing hydrophilic processing on the surface of the coating resin, friction coefficient of the surface under wet conditions can be reduced; accordingly, the ease of insertion of the guide wire into the human body is enhanced.

Furthermore, it is acceptable for an antithrombogenic coating to be formed on the surface of coating resin. Such an antithrombogenic coating can be formed by, for example, subjecting the surface of the resin to antithrombogenic processing. A preferable method of antithrombogenic processing, comprises steps of graft activation of hydrophobic polymer by light exposure, etc.; coating the surface of the resin with the copolymer made by graft or block polymerization between a hydrophilic monomer and a graft activated hydrophobic polymer described above; and that heparin or its salt be ion bonded after drying.

PVC, methyl methacrylate, styrene, acrylonitrile, vinyl acetate, and glycidl methacrylate, etc. are used as the hydrophobic polymer. In terms of the hydrophilic monomer, vinyl compounds, divinyl compounds, cyclic ether compounds, and cyclic imine compounds etc. are used.

By subjecting the surface of the coating resin to antithrombogenic processing, the safety of the guide wire can be improved.

Meanwhile, it is preferable that the surface of the metal wire in the operation section be coated with a thin film of fluororesin or silicon, which affect the human body little. By coating with fluororesin or silicon in this way, handling of the operation section in the guide wire can be improved, and in addition, exotherming of the operation section can be prevented during ablation by high frequency wave.

Although the above-described guide wire is effective as a support member for the catheter, in cases where the target affected area is in the lower left ostium of pulmonary vein or the lower right ostium of pulmonary vein, it does not function to guide the balloon to said area and to promote contact therebetween. The stylet shown in FIG. 16 and FIG. 17 constitutes a support member for a catheter effective in such a situation.

Figure 16:
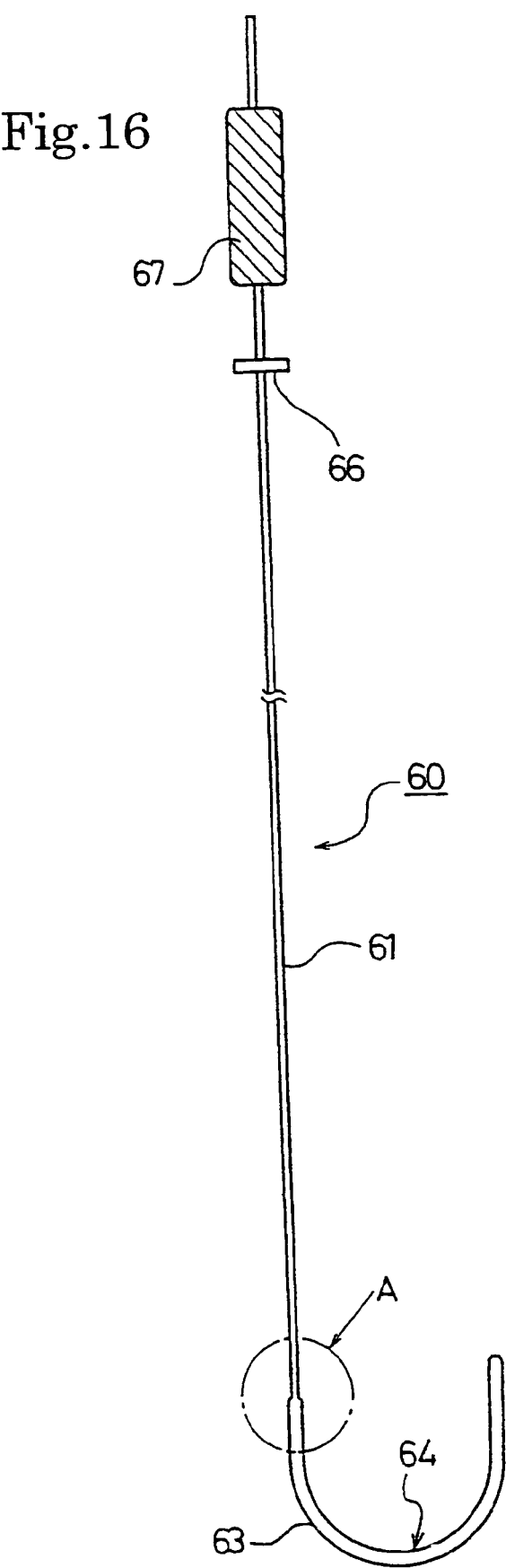
FIG. 16 is a cross-section view showing a stylette used in a catheter for use in the treating of arrhythmia in accordance with the present invention and excluding the intermediate portion thereof
Figure 17:
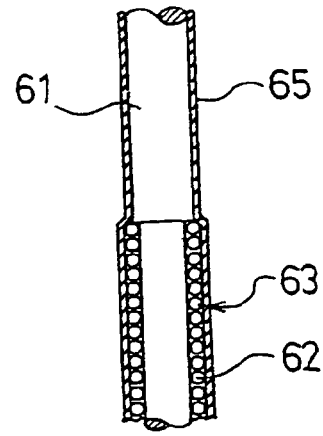
FIG. 17 is an enlarged view of section A shown in FIG. 16.

A core wire 61 comprising a metal with shape memory and radiation shielding properties extends over the full length of the stylet 60 shown in FIG. 16 and FIG. 17. The tip of this core wire 61 is fabricated so as to have a smaller diameter than the rear section, and a coil section 63 fabricated from metal wire 62 with radiation shielding properties coats the outside thereof and is secured thereto by welding. In addition, the tip coated by the coil section 63 is formed as a preliminary deformed portion 64. Furthermore, the entire stylet 60 is coated with a coating material 65, and a stopper 66 and turning handle 67 are provided in the rear section.

Although the above-described preliminary deformed portion 64 has a curved condition when unloaded, it can easily extend into a straight-line configuration under the influence of external force, and furthermore, it is capable of returning elastically to its original curved shape when the external force is removed. In order to easily realize this characteristic of alternating straight-line extension and curved elastic return, the core wire 61 of the preliminary deformed portion 64 has a smaller diameter than the rear end and deflects easily; furthermore, by providing a coil 63 on the outer surface thereof, the curved shape can be easily retained.

Figure 18:
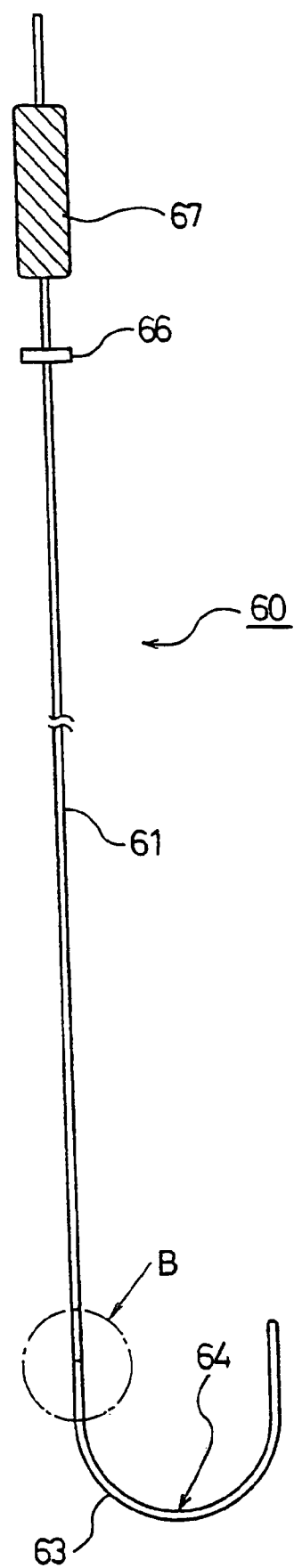
FIG. 18 is a cross-section view showing another embodiment of a stylette used in a catheter for use in the treating of arrhythmia in accordance with the present invention and excluding the intermediate portion thereof.
Figure 19:
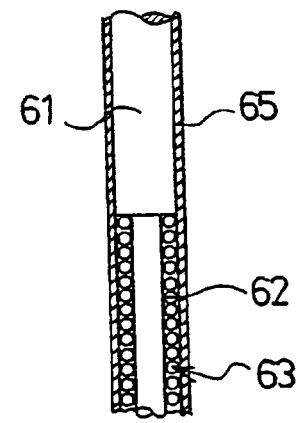
FIG. 19 is an enlarged view of section B shown in FIG. 18.

In the above-described embodiment, the outer diameter of the coil 63 is larger than the outer diameter of the rear end of the core wire 61; however, in the stylet 60 in the embodiment of FIG. 18 and FIG. 19, the outer diameter of the coil 63 is identical to the outer diameter of the rear end of the core wire 61, and all other configuration aspects are identical.

Figure 20:
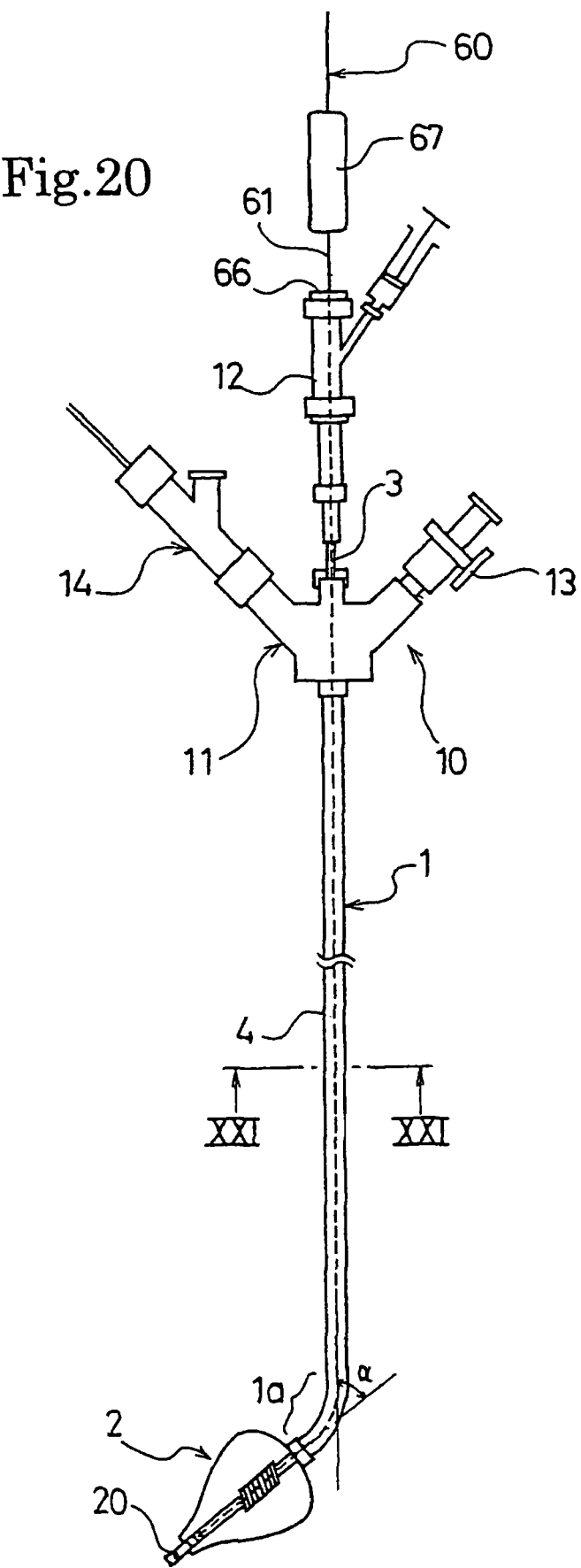
FIG. 20 is a schematic view showing the condition upon insertion of the stylette into a catheter for use in the treating of arrhythmia in accordance with a further embodiment of the present invention.
Figure 21:
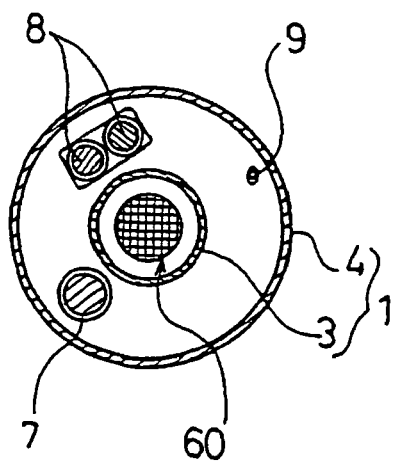
FIG. 21 is a cross-section taken in the plane XXI-XXI shown in FIG. 20.

The above-described stylet 60 is used as shown in FIG. 20 and FIG. 21 as a support member for the catheter. The catheter provides the basic configuration of a catheter for use in the treating arrhythmia according to the present invention, and in addition, provides a flexible section 1a in the vicinity of the tip of the catheter shaft 1 whereto a balloon 2 is attached. The flexible section 1a is processed so as to be less rigid than the body of the catheter shaft 1, and it can easily be deflected. Although no specific requirements apply to the processing method for the flexible section 1a, this can be achieved by, for example, reduction of material thickness through the dissolution of a portion of the material of the outer shaft 4 by using an organic solvent, combination with a low-rigidity tube disposed therebetween, or by increasing the ratio of plasticizer.

In the catheter having the above-described configuration, the axial directions of the catheter shaft 1 and the balloon 2 are identical when the stylet 60 is not inserted. However, when the preliminary deformed portion 64 at the tip of the stylet 60 is extended to a straight-line configuration, the stylet 60 is inserted into the catheter's inner shaft 3 from the rear end, and the preliminary deformed portion 64 is inserted from the flexible section 1a to the tip of the balloon 2, as shown in FIG. 20, the flexible section 1a is deflected by the elastic return force of the preliminary deformed portion 64, and the axial direction of the balloon 2 is inclined at an angle α with respect to the axial direction of the catheter shaft 1.

The ability to incline the balloon 2 ensures that, even when the target affected area is in the lower left ostium of pulmonary vein or the lower right ostium of pulmonary vein etc., the balloon 2 can be accurately guided to the affected area and a close contact can be realized therebetween. Furthermore, by providing the stylet 60 with a suitable degree of rigidity, it is possible to augment the rigidity of the catheter shaft, improving the performance thereof.

Furthermore, by inserting the stylet 60 into the catheter's inner shaft 3 as described, a clearance is formed between the stylet 60 and the inner shaft 3, and physiological saline, grape sugar solution, blood, and other liquids with a viscosity of 5 mPa·s or less flowing through this clearance can be drawn in or charged via the tube 20 of the balloon 2 tip at a speed of approximately 5 to 15 ml/minute.

In the above-described stylet, it is acceptable for the core wire to comprise any metal with high rigidity, shape memory, and radiation shielding properties; however, stainless steels are preferably used. In particular, SUS302, SUS304, and SUS316 are preferable, and in terms of tensile strength, it is acceptable for this material to be of class A through C as set forth in JIS G 4314, with class B being preferable.

In terms of the outer diameter of the core wire 61, it is preferable that this be between 0.5 and 1.5 mm at the straight-shaped end section; furthermore, in the preliminary deformed portion 64 at the tip, a smaller diameter than that of the end section is preferable as a means of achieving greater flexibility. The metal wire 62 forming the coil 63 can be any metal with radiation shielding properties; however, it is preferable that either stainless steels or platinum are preferably used. The diameter of the metal wire 62 of the coil 63 is approximately 0.1 mm, and this coil is wound about the small-diameter section of the core wire 61 in order to achieve close contact therewith. It is preferable that the outer diameter of the coil 63 be between 0.5 and 1.5 mm, and as shown in the example of FIG. 19 in particular, it is preferable that this diameter be the same as the outer diameter of the end section.

Both ends of the metal wire 62 of the coil 63 are welded to the core wire 61. Furthermore, the tip of the coil 63 is processed with a spherical shape so as not to damage the walls of blood vessels etc. when contact is made therewith. Although the length of the coil 63 is determined based on the length of the small-diameter section of the core wire 61, it is preferable that this be between 50 and 150 mm. The coil 63 is providing so that the curved shape of the preliminary deformed portion 64 can be maintained and elastic return can be easily achieved; however, it is acceptable for this member to be formed using braided wire.

It is preferable that the curved shape of the preliminary deformed portion 64 have a rounded L-shape or a J-shape; however, this restriction does not apply if, when inserted into the flexible section 1a of the catheter shaft 1, the angle a between the axial direction of the catheter shaft 1 and the axial direction of the balloon 2 is between 40° and 140° range.

It is preferable that coating material 65 be provided on some or all of the stylet 60. This coating material 65 enables easy sliding of the stylet 60 within the catheter's inner shaft 3, reduces the resistance to insertion therein, and improves operability when selecting the target affected area; furthermore, it also has the effect of reducing conductance to the stylet 60 due to the high frequency waves used during ablation etc.

It is preferable that the coating material 65 be a resin with a low specific inductive capacity, and specifically, has a specific inductive capacity of 3 or less at a frequency of 1 MHz. For example, fluororesin (i.e., (polytetrafluoroethylene, polytetrafluoroethylene hexafluoro-propylene copolymers), polyethylene, polyimide resin, polyamide resin, thermoresin elastomerspolypropylene, and methylpentene polymers, etc. are identified as low specific inductive capacity resin for use as the coating material. Furthermore, it is acceptable for hydrophilic resins, etc. including —OH, —CONH$_2$, —COOH, and NH$_2$ hydrophilic radicals to be secured as a means of imparting low friction properties to the coating material.

A stopper 66 is provided on the rear end of the stylet 60 for fixing position upon insertion into the body. The stopper 66 provided an acurate position of inserted of the preliminary deformed portion 64 with respect to the catheter within for the flexible section 1a and the balloon 2. This stopper 66 is formed so as to be larger than the insertion port of the operation section 10; accordingly, stopping at the specified position becomes possible.

Furthermore, a rotating handle 67 is provided further back than the stopper 66 at the rear end section of the stylet 60. With the stylet 60 inserted into the inner shaft 3 and the balloon 2 in a condition of inclination at the tip of the catheter shaft 1, if the stylet is rotated about the axis thereof by applying torque to the handle 67, the orientation of the balloon about the catheter shaft 1 can be changed. By changing not only the angle of inclination of the balloon 2 but also the orientation thereof in this way, the balloon 2 can be brought into precise contact with the affected area. The handle 67 may be of any shape that does not slip upon the application of torque and that is easily operated. For example, a discoidal or cylindrical shape etc. is preferable.

What is claimed is:

1. A catheter for the treatment of arrhythmia; comprising a catheter shaft having a double-cylinder structure in which an inner shaft is slidably inserted into an outer shaft, a balloon attached between the tip portion of the inner shaft and the tip portion of the outer shaft in a straddling state, a pair of high frequency current-carrying electrodes of which at least one electrode is disposed inside the balloon, and a temperature sensor monitoring the temperature inside the balloon; wherein the catheter is configured such that a tube that is softer than the inner shaft is provided at the tip portion of the inner shaft, and a pipe having radiation shielding properties is connected to the tips of the inner shaft and the outer shaft respectively, and that the balloon is straddled between the radiation shielding pipes.

2. A catheter for the treatment of arrhythmia; comprising a catheter shaft having a double-cylinder structure in which an inner shaft is slidably inserted into an outer shaft, a balloon attached between the tip portion of the inner shaft and the tip portion of the outer shaft in a straddling state, a pair of high frequency current-carrying electrodes of which at least one electrode is disposed inside the balloon, and a temperature sensor monitoring the temperature inside the balloon; wherein the catheter is configured such that a tube that is softer than the inner shaft is provided at the tip portion of the inner shaft, and an anti-elongation string in parallel with the axial direction of the outer shaft, the tip of the anti-elongation string is secured to the tip of the outer shaft, and the rear end of the anti-elongation string is secured to an operation section provided at the rear end of the outer shaft.

3. The catheter for the treatment of arrhythmia of claim 2, further characterized in that the anti-elongation string comprises a line body made of at least one of polyimide fiber, polyester fiber, polyethylene fiber, carbon fiber, and aramid fiber.

* * * * *